United States Patent
Mundy

(10) Patent No.: US 6,492,333 B1
(45) Date of Patent: Dec. 10, 2002

(54) TREATMENT OF MYELOMA BONE DISEASE WITH PROTEASOMAL AND NF-$_\kappa$B ACTIVITY INHIBITORS

(75) Inventor: Gregory R. Mundy, San Antonio, TX (US)

(73) Assignee: Osteoscreen, Inc., San Antonio, TX (US)

( * ) Notice: Subject to any disclaimer, the term of this patent is extended or adjusted under 35 U.S.C. 154(b) by 0 days.

(21) Appl. No.: 09/289,229

(22) Filed: Apr. 9, 1999

(51) Int. Cl.$^7$ .......................... A61K 38/00; A61K 31/16
(52) U.S. Cl. ............................ 514/18; 514/12; 514/13; 514/613; 514/617
(58) Field of Search .............................. 514/12, 18, 13, 514/613, 617

(56) References Cited

U.S. PATENT DOCUMENTS 5,780,454 A    7/1998    Adams et al. ................. 514/64

FOREIGN PATENT DOCUMENTS

| WO | WO 96 32105 A | 10/1996 |
| WO | WO 97 09877 A | 3/1997 |
| WO | WO 98 09620 A | 3/1998 |
| WO | WO 99 58674 A | 11/1999 |
| WO | WO 00 02548 A | 1/2000 |

OTHER PUBLICATIONS

The Merck Manual; Sixteenth Edition; pp. 2256–2260, 1993.*
Feinman R. et al. (1998). *Blood* 92(10) Suppl. 1 part 1–2, 637A.
Ozaki K. et al. (1997). *FEBS LETT* 410(2–3):297–300.
Roodman G.D. (1997). *Cancer* 80 (8 suppl):1557–1563 (abstract).
Sokoloski J.A. et al. (1998). *Cancer Letters* 125(1–2):157–164.
Yu Sheu M. et al. (1997). *Biochemical J* 328(2):363–369.
Alsina et al. "Development of an Vivo Model of Human Multiple Myeloma Bone Disease", Blood (1996) 87(4):1495–1501.
Baeurele et al. "NF–$\kappa$B: Ten Years After", Cell (1996) 87:13–20.
Barnes et al. "Nuclear Factor–$\kappa$B–A Pivotal Transcription Factor in Chronic Inflammatory Diseases", New England Journal of Medicine (1997) 336:1066–1071.
Bataille et al. "Biological Effects of Anti–Inerleukin–6 Murine Monoclonal Antibody in Advanced Muliple Myeloma", Blood (1995) 86(2):685–91.
Bataille et al. "Mechanisms of Bone Lesions in Multiple Myeloma", Hematology/Oncology Clinics of North America (1992) 6:285–295.
Bataille et al. "Serum Levels of Interleukin 6, a Potent Myeloma Cell Growth Factor, as a Reflect of Disease Severity in Plasma Cell Dyscrasias", J Clin Invest (1989) 84:2008–2011.
Baumeister et al. "The Proteasome: Paradigm of a Self–Compartmentalizing Protease", Cell (1998) 92:367–380.
Boyce et al. "Bolus Injections of Recombinant Human Interleukin–1 Case Transient Hypocalcemia in Normal Mice", Endocrinology (1989) 125:2780–2783.
Dallas et al. "Ibandronate Reduces Osteolytic Lesions but not Tumor Burden in a Murine Model of Myeloma Bone Disease", Blood 93:5 (1998) 1697–1706.
Epstein J. "Myeloma Phenotype: Clues to Disease Origin and Manifestation", Hematology/Oncology Clinics of North America (1992) 6:249–256.
Figueiredo–Pereira, M.E. et al. "A New Inhibitor of the Chymotrypsin–Like Activity of the Multicatalytic Proteinase Complex (20S Proteasome) Induces Accumulation of Ubiquitin–Protein Conjugates in a Neuronal Cell", J Neurochem (1994) 63:1578–1581..
Franzoso et al. "Requirement for NF–$\kappa$B in Osteoclast and B–Cell Development", Genes and Development (1997) 11:3482–3496.
Garrett et al. "A Murine Model of Human Myeloma Bone Disease", Bone (1997) 20(6):515–20.
MacDonald et al. "Effects of Human Recombinant CSF–GM and Highly Purified CSF–1 on the Formation of Multinucleated Cells With Osteoclast Characteristics in Long–Term Bone Marrow Cultures", J Bone Miner Res (1986) 1:227–233.
Manning et al. "A Model of Multiple Myeloma: Culture of 5T33 Murine Myeloma Cells and Evaluation of Tumorigenicity in the C57BL/KaLwRjj Mouse", Br J Cancer (1992) 66:1088–1093.
Mundy et al. "Bone Destruction and Hypercalcemia in Plasma Cell Myeloma", Seminar Oncology (1986) 3:291.
Orlowski, RZ, et al. "Tumor Growth Inhibition Induces in a Murine Model of Human Burkitt's Lymphoma by a Proteasome Inhibitor", Cancer Research (1998) 58:4342–4348.
Radl et al. "Multiple Myeloma", American Journal of Pathology (1988) 132:593–597.
Siebenlist et al. "Structure, Regulation and Function of NF–$\kappa$B", Annual Rev Cell Biol (1994) 10:405–455.
Vinitsky, A. et al. J Biol Chem (1994) 269:29860–29866.
Wojcik, C. et al. "Ubiquitin Mediated Proteolysis Centers in HeLA cells: Indication from Studies of an Inhibitor of the Chymotrypsin–like Activity of the Proteasome", European Journal Cell Biol (1996) 71:311–318.
Yoneda et al. "Three cases of Oral Squamous Cancer Associated with Leukocytosis Hypercalcemia, or both", Oral Surgery, Oral Medicine, Oral Pathology (1989) 68:604–611.

* cited by examiner

*Primary Examiner*—Theodore J. Criares
(74) *Attorney, Agent, or Firm*—Morrison & Foerster LLP

(57) ABSTRACT

The present invention involves the identification and use of compositions for treating myeloma bone disease. The compositions inhibit proteasomal activity and decrease the activity of the transcription factor NF-$\kappa$B. Assessment of a candidate compound for its ability to inhibit production or activity of proteasomal enzymes or NF-$\kappa$B provides a useful means to identify agents to treat myeloma bone disease.

2 Claims, No Drawings

US 6,492,333 B1

TREATMENT OF MYELOMA BONE DISEASE WITH PROTEASOMAL AND NF-κB ACTIVITY INHIBITORS

TECHNICAL FIELD

The invention relates to compositions and methods for use in treating bone disease associated with myeloma. More specifically, the invention concerns the use of inhibitors of proteasomal and NF-κB activity for this purpose.

BACKGROUND ART

Multiple myeloma is the second most common hematologic malignancy producing some 15,000 new diagnosed cases each year in the United States with the number of existing myeloma patients numbering between 30,000 to 40,000 (Mundy et al. *Seminar Oncol* (1986) 3:291). Eighty percent of whom suffer from devastating osteolytic bone destruction caused by increases in osteoclast formation and activity (Mundy et al. (1986), supra). The associated bone destruction can cause severe bone pain, pathologic fractures, spinal cord compression, and life-threatening hypercalcemia. It has been reported that multiple myeloma cannot be cured by standard chemotherapy or stem cell transplantation (Attai et al. *Blood* (1996) 87(4):1495–1501).

Myeloma bone disease results in severe morbidity and potential mortality. Accordingly, the development of strategies and treatments that control the osteolytic bone destruction resulting in these patients has become of vital importance.

However, the pathologic mechanisms responsible for increased osteoclast activity in multiple myeloma patients are unknown. Further, the accompanying bone lesions that occur in the patients take on several pattern forms. Occasionally, patients develop discrete osteolytic lesions in association with solitary plasmacytomas. Other patients have diffuse osteopenia, which mimics the appearance of osteoporosis, and results from the diffuse dispersion of the myeloma cells throughout the axial skeleton. In most atients, there are multiple discrete lytic lesions occurring adjacent to nests of myeloma ells. Hypercalcemia occurs as a consequence of bone destruction in about one third of atients with advanced bone disease. Rarely do patients with myeloma fail to develop lytic lesions or bone loss, instead they have an increased new bone formation around myeloma cells. This rare situation is known as osteosclerotic myeloma.

Osteolytic bone lesions are the most common deleterious skeletal manifestation in patients with myeloma. Although the precise molecular mechanisms remain unclear, nevertheless observations over 15 years have revealed several facts. First, the mechanism by which bone is destroyed in myeloma occurs via the osteoclast, the normal boneresorbing cell. Second, osteoclasts accumulate on boneresorbing surfaces in myeloma adjacent to collections of myeloma cells. Thus, it appears that the mechanism by which osteoclasts are stimulated in myeloma is a local one. Third, it has been known for many years that cultures of human myeloma cells, in vitro, produce several osteoclastactivating factors, including lymphotoxin, interleukin-1 (IL-1), and interleukin-6 (IL-6). Fourth, hypercalcemia occurs in approximately one third of patients with myeloma at some point during the course of the disease. Hypercalcemia is always associated with markedly increased bone resorption, and frequently with the impairment in glomerular filtration. Fifth, the increase in osteoclastic bone resorption in myeloma is usually associated with a marked impairment in osteoblast function. Alkaline phosphatase activity in the serum is decreased or remains in the normal range, in contrast to patients with other types of osteolytic bone disease. Also, radionuclide scans do not show evidence of increased uptake, which indicates impaired osteoblast response to the increase in bone resorption.

Various mediators have been implicated in the stimulation of osteoclast activity in patients with multiple myeloma, including lymphotoxin (tumor necrosis factor-β (TNFβ)), interleukin-1-beta (IL-1β), parathyroid hormone-related protein (PTHrP), and interleukin-6 (IL-6). However, reports of factors that are produced by myeloma cells have been wholly inconsistent. Some studies have been inconclusive due to the presence of other contaminating cell types including stromal cells and macrophages in the multiple myeloma cell population. IL-6 is a major myeloma growth factor that enhances the growth of several myeloma cell lines and those cells freshly isolated from myeloma patients (Bataille et al. *J Clin Invest* (1989) 84:2008). IL-6 production can be detected in about 40% of freshly isolated myeloma cells by PCR, but only 1 in 150 patients studied show detectable IL-6 production by immunocytochemistry or ELISA assays (Epstein J. *Hematology/Oncology Clinics of North America* (1992) 6:249–256. The IL-6 receptors were only detected in 6 of 13 samples from patients with multiple myeloma (Bataille et al. *Hematology/Oncology Clinics of North America* (1992) 6:285–295). Furthermore, mature myeloma cells have been reported to have a minimal proliferative response to interleukin-6. Interleukin-11 (IL-11) has an IL-6-like activity on plasmacytomas, but to date no one has demonstrated that myeloma cells produce IL-11. Bataille and coworkers (Bataille et al. *Blood* (1995) 86(2):685–91) have shown that the perfusion of 5 patients with refractory myeloma with an antibody of IL-6 decreased the size of the myeloma cell burden in only 2 of these patients.

In addition to IL-6 and IL-1β, TNFα and lymphotoxin have been implicated as mediators of bone destruction in multiple myeloma. IL-6 is an extremely potent boneresorbing agent that induces hypercalcemia in animal models in the absence of renal failure (Boyce et al. *Endocrinology* (1989) 125:2780–2783). In contrast, hypercalcemia rarely occurs in myeloma patients without renal failure. More importantly, in highly purified myeloma cells, no IL-1β and only rare TNFα production can be detected, suggesting that other contaminating cell types such as macrophages may be the source of the IL-1β and TNFα (Epstein (1992), supra). Similarly, lymphotoxin is produced by most human myeloma cell lines (Bataille et al. (1995), supra) but does not appear to be produced by myeloma cells in vivo (Alsina et al. *Blood* (1996) 87(4):1495–1501). In addition to IL-1β, TNFα, lymphotoxin and IL-6, myeloma cells produce a truncated form of M-CSF which is biologically active. However, M-CSF does not cause hypercalcemia or induce osteoclast formation by itself in human marrow cultures (MacDonald et al. *J Bone Miner Res* (1986) 1:227–233). Thus, the specific role played by many of these factors in osteolytic bone disease occurring in myeloma patients has not been definitively illustrated in vivo. Thus, the known cytokines do not entirely account for the bone resorption observed in these patients.

Furthermore, freshly isolated marrow supernatants from the affected bones in myeloma patients contain a boneresorbing activity that comprises an unknown resorbing cytokine. These data suggest that myeloma cells produce factors in the marrow microenvironment that differ from those produced by the cells in vitro and that this factor(s) is not a cytokine previously known to be produced by myeloma cells.

NF-κB is a transcription factor which regulates the expression of the kappa light chain gene in murine B lymphocytes, but is now known to be expressed ubiquitously. A number of different NF-κB proteins have been identified and well-characterized (Siebenlist et al. *Annu Rev Cell Biol* (1994) 10:405–455; see also, Baeurele et al. *Cell* (1996) 87:13–20). NF-κB in its active state is a heterodimer, which consists usually of two subunits. The most common subunits are known as P65 and P50; another common subunit is P52. Different combinations of these subunits may be involved in the observation of different target genes. In unstimulated cells, NF-κB is both present in the cytoplasm and bound to other proteins known as IkBα and IkBβ and prevent it from entering the nucleus. Upon stimulation of cells, specific enzymes lead to the phosphorylation of IkB, which in turn leads to its rapid degradation in the proteasomes. Upon degradation of IkB, NF-κB is then available to translocate to the nucleus. In the nucleus, NF-κB binds to promoter sequences of target genes and leads to their transcription. Proteasome activity is thus required for NF-κB translocation.

The proteasome is a non-compartmentalized collection of unrelated proteases which form a common architecture in which proteolytic subunits are self-assembled to form barrel-shaped complexes (Baumeister et al. *Cell* (1998) 92:367–380). The proteasome contains an array of distinct proteolytic activities inside eukaryotic cells; among these are activities that assist in translocating NF-κB to the nucleus where it exerts its effect. Compounds which inhibit proteasomal activity reduce NF-κB activity by limiting its capacity to be translocated to the nucleus (Barnes et al. *New Engl J Med* (1997) 336:1066–1071).

It has recently been shown that mice lacking expression of the transcription factor NF-κB develop abnormal bone conditions, such as osteopetrosis—the converse of osteoporosis—due to an absence of osteoclast formation (Franzoso et al. *Genes and Dev* (1997) 11:3482–3496). Osteopetrosis is characterized by absence of osteoclast function, along with the filling in of the marrow cavity with osteocartilagenous material. However, the mechanisms of osteoclast formation in normal mice as compared to such formation in myeloma are different; the cytokine pattern characterizing osteoclast formation in myeloma has not been characterized. As the mechanisms are different, it is unpredictable what the effect of NF-κB gene depletion would be on myeloma bone disease.

Orlowski, R Z, et al, *Cancer Res* (1998) 58:4342–4348 have shown that lymphoma tumor growth is inhibited by a proteasome inhibitor. However, the etiologies of lymphoma and of myeloma are quite different, and it would not be predictable whether agents effective against one would or would not be effective against the other.

DISCLOSURE OF THE INVENTION

The present invention adds to the repertoire of agents which inhibit myeloma bone disease by providing drugs that will inhibit key proteins and enzymes involved in proteasomal activity and which decrease the activity of the nuclear transcription factor NF-κB, and thus inhibit the bone disease associated with myeloma. In accordance with the present invention, inhibition of the functions of proteasomal proteins and of the transcription factor NF-κB in myeloma cells leads to decreased myeloma bone disease. Thus, assessing a candidate compound for its ability to inhibit proteasomal proteins or NF-κB provides a useful means to identify agents to treat myeloma bone disease.

Thus, in one aspect, the invention provides methods to identify compounds that are useful to treat myeloma bone disease by assessing their capacity to inhibit proteasome activity or to inhibit the activity of the transcription factor NF-κB, or to inhibit production of these moieties. In another aspect the invention provides a method to treat myeloma bone disease by administering to a subject in need of such treatment a compound that inhibits proteasome activity, the activity of transcription factor NF-κB, or the production of the proteasome enzymes or NF-κB.

MODES OF CARRYING OUT THE INVENTION

In accordance with the present invention, there are provided methods of treating bone disease associated with myeloma in subjects suffering therefrom. The method comprises administering to the subject, in a sufficient amount, a compound which inhibits proteasomal activity and function, or the activity of the nuclear transcription factor NF-κB, or the production of these proteins.

As employed herein, the term "subject" embraces human, as well as other animal species, such as, for example, canine, feline, bovine, porcine, rodent, and the like.

As used herein, the terms "treat" or "treatment" include a postponement of development of bone disease symptoms and/or a reduction in the severity of such symptoms that will, or are expected to develop. Thus, the terms denote that a beneficial result has been conferred on a vertebrate subject with myeloma bone disease.

The compositions of the invention may be administered systemically or locally. For systemic use, the compounds herein are formulated for parenteral (e.g., intravenous, subcutaneous, etc.) delivery according to conventional methods. Intravenous administration can be by a series of injections or by continuous infusion over an extended period of time. Treatment will continue until the desired outcome is achieved. In general, pharmaceutical formulations will include a compound of the present invention in combination with a pharmaceutically acceptable vehicle.

Parenteral preparations comprise particularly sterile or sterilized products. Injectable compositions may be provided containing the active compound and any of the well known injectable carriers. These may contain salts for regulating the osmotic pressure.

Within the present invention, an "effective amount" of a composition is that amount which produces a statistically significant effect. For example, an "effective amount" for therapeutic uses is the amount of the composition comprising an active compound herein required to provide a clinically significant decreases in the viability of human myeloma cells or reduces tumor markers in the sera obtained from the affected subjects. Such effective amounts will be determined using routine optimization techniques and are dependent on the particular condition to be treated, the condition of the patient, the route of administration, the formulation, and the judgment of the practitioner and other factors evident to those skilled in the art. The dosage required for the compounds of the invention is manifested as a statistically significant difference in tumor volume, delay of onset of limb paralysis or tumor marker indicia between treatment and control groups. General guidance for treatment regimens is obtained from experiments carried out in animal models of the disease of interest.

The dosage of the compounds of the invention will vary according to the extent and severity of the need for treatment, the activity of the administered compound, the general health of the subject, and other considerations well known to the skilled artisan.

The compounds useful in the methods and compositions of the invention are inhibitors of proteasomal activity or of the transcription factor NF-κB. Known inhibitors of these activities can be ascertained from the literature and compounds can be tested for these activities using assays known in the art. In addition, inhibitors which lower the level of effective expression of the nucleotide sequence encoding the enzymes that have proteasomal activity or of the nucleotide sequence encoding NF-κB can be assessed and used in the invention methods.

Examples of compounds useful in the invention are as follows:

In the foregoing list, lactacystin is known to be an irreversible inhibitor of proteasome activity. It binds to the β catalytic subunit and is a specific inhibitor of the 20S proteasome. It also irreversibly inhibits NF-κB.

SN50 is the NLS (nuclear localization sequence) of p50 plus the hydrophobic region of K-FGF. It inhibits the translocation of the NF-κB active complex to the nucleus.

Certain peptidyl epoxy ketones such as EST are irreversible inhibitors of the proteasomes. MG-132 shows activity against the chymotryptic activity of the 20S protein without affecting its ATPase or isopeptidase activity and reversibly inhibits NF-κB activity. MG-115 and MG-341 show similar

| Proteasome Inhibitors | |
|---|---|
| PSI | N-carbobenzoyl-Ile-Glu-(OtBu)-Ala-Leu-CHO |
| MG-132 | N-carbobenzoyl-Leu-Leu-Leu-CHO |
| MG-115 | N-carbobenzoyl-Leu-Leu-Nva-CHO |
| MG-101 or Calpain Inh I | N-Acetyl-Leu-Leu-norLeu-CHO |
| ALLM | N-Acetyl-Leu-Leu-Met-CHO |
| | N-carbobenzoyl-Gly-Pro-Phe-Leu-CHO |
| | N-carbobenzoyl-Gly-Pro-Ala-Phe-CHO |
| | N-carbobenzoyl-Leu-Leu-Phe-CHO |
| | N-carbobenzoyl-Leu-Ala-Leu-CHO |
| Gliotoxin | [structure] |
| SN50 | NLS of NF-κB MW 2781 |
| Bay 11-7082 | [structure] |
| Capsaicin | [structure] |
| PDTC | [structure] |
| PPM-18 | [structure] |

See, for example, Vinitsky, A. et al. *J Biol Chem* (1994) 269:29860–29866; Figueiredo-Pereira, M. E. et al. *J Neurochem* (1994) 63:1578–1581; Wojcik, C. et al. *Eur J Cell Biol* (1996) 71:311–318.

activities to MG-132. Various other inhibitors of NF-κB are less active in the ABA assay. These include capsaicin, curcumin, and resiniferatoxin. Other compounds known to inhibit NF-κB are gliotoxin and PDTC (1-pyrrolidine carbothiotic acid). Various other compounds such as BAY-11-7082 and BAY-11-7085 as well as calyculin-A inhibit phosphorylation of NF-κB. Calpain inhibitor inhibits calpain 1 and the proteasome; other compounds such as olomoucine and roscovitine inhibit cdk2 and/or cdk5.

Compounds which inhibit the production of the enzymes having proteasomal activity or of NF-κB can be assessed by measuring the level of production of these proteins in the presence and absence of candidate compounds. The levels of production can be readily measured in in vitro systems using, for example, immunoassays for the level of protein produced. The levels of such proteins can also be assessed by utilizing, for example, methionine labeling and size separation of proteins in the cells to be assessed. In order to effect a convenient level of protein production for measurement, it is advantageous to use recombinant expression systems for the relevant enzymes or the NF-κB so that substantial amounts are produced.

Typical approaches to inhibiting the production of NF-κB or proteasome enzymes include the use of antisense technology or the formation of triplexes with double-stranded forms of nucleotide sequences relevant in the expression of the genes. In addition, various small molecules may also inhibit this production.

Preparation A

Models of Human Myeloma Bone Disease

Radl et al. (*Am J Pathol* (1988) 132:593–597) described a murine model of myeloma which occurred spontaneously in aging mice of the C57 BL/KaLwRij strain. This condition occurred upon aging in approximately one (1) mouse of this strain for every two-hundred (200), and led to a monoclonal gammopathy with all of the characteristic features of the human disease, including growth of malignant cells in the bone marrow and characteristic skeletal lesions. Id. By transplantation of the fresh or frozen myeloma cells by intravenous injection into recipients of the same strain, the disease can be produced more precisely. More recently, Manning et al. (*Br J Cancer* (1992) 66:1088–1093) described a cell line derived from one of these myelomas.

To develop a better animal model of human myeloma bone disease, a cell line was established and subcloned from this murine myeloma by Garrett et al. *Bone* (1997) 20(6):515–20. This cell line (ST33) causes osteolytic bone lesions in mice characteristic of human myeloma bone disease. Osteolytic lesions were determined by animal x-rays and quantified. The cell line produces IL-6, but grows independently of exogenous IL-6. Mice inoculated intravenously with the cultured cells predictably develop an identical disease to the mice injected intravenously with fresh bone marrow-derived myeloma cells, including monoclonal gammopathy and radiologic bone lesions. Some of the mice became hypercalcemic, and the bone lesions are characterized by increased osteoclast activity. Identical results were obtained in inoculated Nu/Bg/XID mice with cultured murine myeloma cells.

This model is used to determine the mechanisms by which the myeloma cells cause osteoclast activation, since mice can be inoculated with a precise numbers of cells and it can accurately be predicted when the mice will develop bone lesions, paraplesia, and become hypercalcemic.

It has been recently shown that transfer of cells derived from other 5T myelomas such as 5TGM-1 into inbred C57BL/KaLwRij strain of mice reliably produce myeloma bone disease with involvement of non-bone organs such as the liver and kidney. The animals have elevated serum levels of IgG2b. 5TGM-1 cells are IL-6 independent. More recently the role of adhesion molecules in the induction of bone-resorbing cytokines by these myeloma cells in vitro was demonstrated.

5TGM-1 myeloma cells were initially derived from a myeloma, designated 5TGM-1, which arose spontaneously in an aged C57BL/KaLwRij mouse, as reported by Dallas et al. (to be published in *Blood* (1998)). 5TGM-1 cells were propagated from the bone marrow of this mouse, maintained in Iscove's Modified Dulbecco's Medium™ ("IMDM", available at Life Tech. Inc, Gaithersburg, Md.), and supplemented with 10% Fetal Bovine Serum™ ("FBS", Summit, Fort Collins, Colo.) and 1% penicillin-streptomycin solution (GIBCO, Grand Island, N.Y.) at 37° C. in 5% $CO_2$ atmosphere. Bone marrow transfer of 5TGM-1 myeloma in the inbred C57BL/KaLwRij strain of mice also reliably produced myeloma disease exhibiting all the features of human myeloma, such as severe osteolysis and involvement of non-bone organs such as liver and kidney. Based on the histological examination of affected organs in the STGM-1-bearing mice and the increased serum level of monoclonal IgG2b confirmed by SDS-PAGE™, 5TGM1 was defined as a murine myeloma.

Still another model of myeloma bone disease was developed by injecting the human myeloma cell line ARH77 into sublethally irradiated SCID™ mice (Alsina et al. *Blood* (1996), supra). These animals developed hypercalcemia, lytic bone lesions and the histologic finding characteristic of human myeloma.

EXAMPLE 1

Effect of PSI Inoculated Into Subcutaneous Tumors

Nine (9) C57BL/KaLwRij mice were inoculated with $0.5 \times 10^6$ 5TGM-1 cultured myeloma cells which were injected subcutaneously over the flank. Clearly visible tumors developed in six (6) (~70%) of the mice after 2–3 weeks, with tumor volumes being assessed by the following standard formula (Yoneda et al. *Oral Surgery, Oral Medicine, Oral Pathology* (1989) 68:604–611):

$$\text{Tumor volume (cm}^3) = \frac{4/3 \ [(\text{length} + \text{width}) - 1]}{2}$$

The six (6) mice with tumors were randomized into two groups and treatment was commenced on day 35. One group had PSI injected directly into the tumors (~5 mg/kg/day) and the other group had only vehicle injected into the tumors. The tumors in the latter group (untreated mice) continued to grow, resulting in the mice dying between 42 and 55 days after myeloma cell inoculation. The size of the tumors in the treated mice decreased markedly and the mice remained healthy up until 3 months after tumor inoculation, even though treatment was discontinued. The treated mice were alive and well with no signs of tumor 4 months after treatment.

EXAMPLE 2

Effect of PSI Administered Parenterally

Ten (10) C57BL/KaLwRij mice were inoculated intravenously with $1 \times 10^6$ 5TGM-1 cultured myeloma cells. When untreated, the mice invariably develop hind-limb paralysis after 26–30 days.

One group of five (5) mice were injected with PSI (5 mg/kg/day) subcutaneously over their flank portion for 28 days and the other group received only vehicle. The treated mice showed a marked difference in the time required for hind-limb paralysis to develop. All of the untreated mice had developed hind-limb paralysis by at least day 27. In contrast, none of the PSI-treated group developed paraplegia before at least day 33. This is the first time demonstration of which the inventors are aware of has delay the onset of hind-limb paralysis in an in vivo model of human myeloma disease.

EXAMPLE 3

Effect of PSI in vitro

In another experiment, the direct effect of the proteasomal inhibitor PSI and other NF-kB inhibitors on the viability in human myeloma cells and 5TGM-1 cells in vitro was evaluated.

$1 \times 10^6$ human myeloma (IM9 and U266BL) cells or 5TGM-1 cells were plated out in the presence and/or absence of PSI and other NF-κB inhibitors. After 24 hours, the viability of the myeloma cells was assessed by the trypan blue dye-exclusion assay. These compounds, at low (submicromolar) concentrations, markedly decrease the viability of both human and murine myeloma cells in culture.

Both PSI and PDTC are effective in decreasing the viability of human myeloma IM-9 cells to less than 10% at a concentration of 0.1 $\mu$M. PSI causes the cells to exhibit a marked diminution in viability at 0.01 $\mu$M. However, PPM-18 is relatively ineffective.

PSI is quite effective (less than 20% viability) at 0.01 $\mu$M vis-+e,fra a+ee -vis U266BL cells, while PDTC becomes effective (less than 40% viability) at 0.1 $\mu$M. Again, PPM-18 does not appear to affect viability appreciatively as compared to control.

However, with regard to 5TGM1 cells, all three compounds, PSI, PDTC, and PPM-18 are effective in diminishing the viability as compared to control. All three compounds reduce viability to less than 40% at only 1 nM concentration; PSI is able to reduce viability almost to 0 at 100 nM.

EXAMPLE 4

Effect of PSI and PDTC Administered Parenterally

Eight (8) C57BL/KwLaRij mice were each injected with $1 \times 10^6$ 5TGM-1 cells through the tail vein. They were then randomized into two groups, one group dosed with PSI (5 mg/kg/day subcutaneously) and the other group (untreated control) received only vehicle. Sera were obtained at the start (day 0) and on days 7, 14 and 18 followed by assay for IgG2b. The results show that PSI markedly reduced the tumor marker IgG2b, thus indicating its beneficial effect on tumor burden. Similar experiments showed that PDTC at dosages of 100 mg/kg/day which were administered subcutaneously showed similar beneficial effects.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method to treat osteolytic bone destruction resulting from myeloma in a subject comprising administering to a subject in need of such treatment an effective amount of PSI or PPM-18.

2. The method of claim 1 wherein said subject is further characterized by a condition selected from the group consisting of osteopenia, osteolytic lesions, bone fracture and osteolytic bone disease.

* * * * *